US007697657B2

(12) United States Patent
Walter et al.

(10) Patent No.: US 7,697,657 B2
(45) Date of Patent: Apr. 13, 2010

(54) SYSTEM AND METHOD OF DENSITY AND EFFECTIVE ATOMIC NUMBER IMAGING

(75) Inventors: Deborah Joy Walter, Terre Haute, IN (US); Xiaoye Wu, Rexford, NY (US); John Eric Tkaczyk, Delanson, NY (US); Yanfeng Du, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 57 days.

(21) Appl. No.: 11/690,245

(22) Filed: Mar. 23, 2007

(65) Prior Publication Data
US 2008/0273666 A1 Nov. 6, 2008

(51) Int. Cl.
*A61B 6/00* (2006.01)
(52) U.S. Cl. .............................. 378/4; 378/5
(58) Field of Classification Search .............. 378/4, 378/9, 5
See application file for complete search history.

(56) References Cited

U.S. PATENT DOCUMENTS

| 4,029,963 | A | * | 6/1977 | Alvarez et al. ............... 378/5 |
| 4,571,491 | A | * | 2/1986 | Vinegar et al. ........... 250/252.1 |
| 4,686,695 | A | * | 8/1987 | Macovski .................. 378/146 |
| 7,190,757 | B2 | | 3/2007 | Ying et al. |
| 2004/0184574 | A1 | * | 9/2004 | Wu et al. .................... 378/5 |
| 2004/0223585 | A1 | * | 11/2004 | Heismann et al. ........... 378/54 |

OTHER PUBLICATIONS

Lehmann et al., Generalized image combinations in dual KVP digital radiography, Med Phys, 8 (5), Sep./Oct. 1981, pp. 659-667.*
Marziani et al., Dual-energy tissue cancellation in mammorgraphy with quasi-monochromatic x-rays, Phys Med Biol, 47, 2002, pp. 305-313.*
Brody et al., A method for selective tissue and bone visualization using dual energy scanned projection radiography, Med Phys, 8 (3), May/Jun. 1981, pp. 353-357.*
Taibi et al., Dual-energy imaging in full-field digital mammography: a phantom study, Phys Med Biol, 48, 2003, pp. 1945-1956.*
Heismann et al., Density and atomic number measurements with spectral x-ray attenuation method, Journal of Applied Physics, vol. 94, No. 3, Aug. 2003, pp. 2073-2079.*
Walter et al., Accuracy and precision of dual energy CT imaging for the quantification of tissue fat content, Medical Imaging, Proceedings of SPIE, vol. 6142, Feb. 2006, pp. 1-12.*

(Continued)

*Primary Examiner*—Chih-Cheng G Kao
*Assistant Examiner*—Alexander H Taningco
(74) *Attorney, Agent, or Firm*—Jason K. Klindtworth

(57) ABSTRACT

A system and method of density and effective atomic number imaging include a computer programmed to acquire projection data from the detector of an unknown material at the time of projection data acquisition. The computer is also programmed to generate a density image for the unknown material based on a calibration of two or more known basis materials and to generate an effective atomic number (Z) for the unknown material based on the calibration of two or more known basis materials and based on a function arctan of a ratio of atomic numbers of the two or more known basis materials. The density and effective atomic number images are stored to a computer readable storage medium.

27 Claims, 3 Drawing Sheets

OTHER PUBLICATIONS

Taguchi et al., Image-domain material decomposition using photon-counting CT, Medical Imaging, Proceedings of SPIE, vol. 6510, 2007, pp. 1-12.*

R.E. Alvarez et al., "Energy-Selective Reconstructions in X-Ray Computerized Tomography," Phys. Med. Biol., 1976, vol. 21, No. 5, 733-744.

* cited by examiner

SYSTEM AND METHOD OF DENSITY AND EFFECTIVE ATOMIC NUMBER IMAGING

BACKGROUND OF THE INVENTION

The present invention relates generally to diagnostic imaging and, more particularly, to a method and apparatus of basis material decomposition and representation of diagnostic imaging data.

Exemplary diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

An exemplary CT imaging system comprises an energy discriminating (ED), multi energy (ME), and/or dual energy (DE) CT imaging system that may be referred to as an EDCT, MECT, and/or DE-CT imaging system. The EDCT, MECT, and/or DE-CT imaging system in an example is configured to be responsive to different x-ray spectra. For example, a conventional third generation CT system acquires projections sequentially at different peak kilovoltage (kVp) level, which changes the peak and spectrum of energy of the incident photons comprising the emitted x-ray beams. Two scans in an example are acquired—either (1) back-to-back sequentially in time where the scans require two rotations around the subject, or (2) interleaved as a function of the rotation angle requiring one rotation around the subject, in which the tube operates at 80 kVp and 160 kVp potentials. Special filters in an example are placed between the x-ray source and the detector such that different detector rows collect projections of different x-ray energy spectra. The special filters that shape the x-ray spectrum in an example can be used for two scans that are acquired either back to back or interleaved. Energy sensitive detectors in an example are used such that each x-ray photon reaching the detector is recorded with its photon energy.

Exemplary ways to obtain the measurements comprise: (1) scan with two distinctive energy spectra, and (2) detect photon energy according to energy deposition in the detector. EDCT/MECT/DE-CT provides energy discrimination and material characterization. For example, in the absence of object scatter, the system derives the behavior at any other energy based on the signal from two regions of photon energy in the spectrum: the low-energy and the high-energy portions of the incident x-ray spectrum. In an exemplary energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials.

The conventional basis material decomposition (BMD) algorithm is based on the concept that, in the energy region for medical CT, the x-ray attenuation of any given material can be represented by a proper density mix of two other materials with distinct x-ray attenuation properties, referred to as the basis materials. The BMD algorithm computes two CT images that represent the equivalent density of one of the basis materials based on the measured projections at high and low x-ray photon energy spectra, respectively. Since a material density is independent of x-ray photon energy, these images are approximately free of beam-hardening artifacts. An operator can choose the basis material to target a certain material of interest, for example, to enhance the image contrast.

An exemplary previous discussion of BMD and analysis of a relation of the x-ray attenuation to effective Z or effective atomic number employed approximate formulas that allow insufficient precision in data prediction other than in cases where pure elements are measured, such as through employment of constrained iteration, polynomial approximations, or calibration with real materials. The resulting error in the formulation is significant when very small differences in atomic number are sought such as where delta Z is a fraction of an atomic number. Furthermore, existing algorithms for the decomposition of energy sensitive data into density and effective Z are mathematically unstable. For materials with very small density such as approaching zero or air, the atomic number is undefined. This fact causes numerical instability resulting in high noise for typical techniques.

Therefore, it would be desirable to design a system and method that enhances accuracy and/or precision for computing the density and effective atomic number in diagnostic x-ray CT.

BRIEF DESCRIPTION OF THE INVENTION

The present invention is directed to a system and method for computing the density and effective atomic number of an unknown material.

According to an aspect of the present invention, a diagnostic imaging system includes a high frequency electromagnetic energy source that emits a beam of high frequency electromagnetic energy toward an object to be imaged, a detector that receives high frequency electromagnetic energy emitted by the high frequency electromagnetic energy source and attenuated by the object, and a data acquisition system (DAS) operably connected to the detector. A computer is operably connected to the DAS and programmed to acquire projection data from the detector of an unknown material at the time of projection data acquisition. The computer is also programmed to generate a density image for the unknown material based on a calibration of two or more known basis materials and to generate an effective atomic number (Z) for the unknown material based on the calibration of two or more known basis materials and based on a function arctan of a ratio of atomic numbers of the two or more known basis materials. The density and effective atomic number images are stored to a computer readable storage medium.

According to another aspect of the present invention, a method of diagnostic imaging includes acquiring multi-energy range x-ray data attenuated by an object comprising an unknown material and separating the multi-energy range x-ray data into at least two energy bins. The method also includes calibrating a plurality of basis materials and determining an arc tangent of a ratio of atomic numbers of the plurality of basis materials. A density image of the unknown material based on the calibration is generated, and an effective Z image of the unknown material based on the calibration and the arc tangent determination is generated. The method includes storing the density and effective Z images to computer memory.

According to yet another aspect of the present invention, a computer readable storage medium includes instructions stored thereon that, when executed by a processor, causes the computer to acquire x-ray projection data of an unknown material and acquire calibration data of a pair of known materials. The instructions further cause the computer to display a reconstructed density image for the unknown material to a user, the density image generated from a reconstruction based on the calibration data and display a reconstructed effective Z image for the unknown material to a user, the effective Z image generated from a reconstruction based on the calibration data and based on arc tangent data of a ratio of atomic numbers of the pair of known materials.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Exemplary diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Exemplary applications of x-ray sources comprise imaging, medical, security, and industrial inspection applications. However, it will be appreciated by those skilled in the art that an exemplary implementation is applicable for use with single-slice or other multi-slice configurations. Moreover, an exemplary implementation is employable for the detection and conversion of x-rays. However, one skilled in the art will further appreciate that an exemplary implementation is employable for the detection and conversion of other high frequency electromagnetic energy. An exemplary implementation is employable with a "third generation" CT scanner and/or other CT systems.

Figure 1:
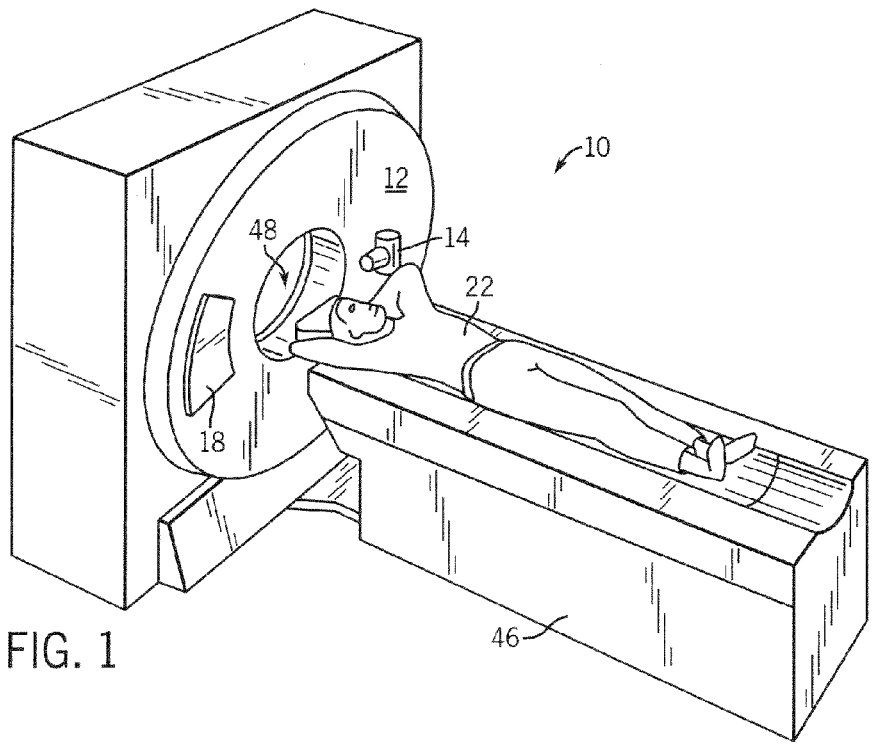
FIG. 1 is a pictorial view of a CT imaging system.
Figure 2:
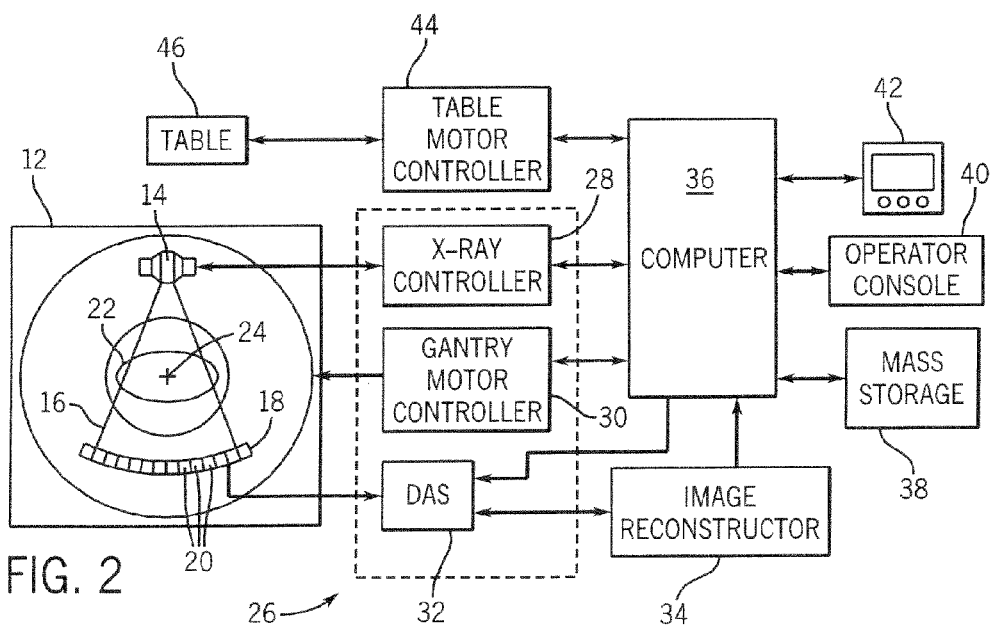
FIG. 2 is a block schematic diagram of the system illustrated in FIG. 1.

Referring to FIGS. 1 and 2, a CT imaging system 10 is shown as including a gantry 12 representative of a "third generation" CT scanner. The CT system 10 in an example comprises an energy discriminating (ED), multi energy (ME), and/or dual energy (DE) CT imaging system that may be referred to as an EDCT, MECT, and/or DE-CT imaging system. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to the x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

EDCT/MECT/DE-CT provides energy discrimination and material characterization. For example, in the absence of object scatter, the system derives the behavior at any other energy based on the signal from two regions of photon energy in the spectrum: the low-energy and the high-energy portions of the incident x-ray spectrum. In an exemplary energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two materials.

An illustrative discussion is now presented in connection with an exemplary implementation of a decomposition algorithm. An image or slice is computed which may incorporate, in certain modes, less or more than 360 degrees of projection data, to formulate an image. The image may be collimated to desired dimensions, using tungsten shutters in front of the x-ray source 14 and different detector apertures. A collimator typically defines the size and shape of the beam of x-rays 16 that emerges from the x-ray source 14. A bowtie filter may be included in the system 10 to further control the dose to the patient 22. An exemplary bowtie filter pre-attenuates the beam of x-rays 16 to accommodate the body part being imaged, such as head or torso, such that, in general, less attenuation is provided for x-rays passing through or near an isocenter of the patient 22. The bowtie filter in an example shapes the x-ray intensity during imaging in accordance with the region of interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

In exemplary EDCT/MECT/DE-CT, two or more sets of projection data are obtained for the imaged object at different tube peak kilovoltage (kVp) levels, which change the peak and spectrum of energy of the incident photons comprising the emitted x-ray beams or, alternatively, at a single tube peak kilovoltage (kVp) level or spectrum with an energy resolving detector of the detector array 18. The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the CT system 10 reveals internal features of the patient 22, expressed in the densities of the three basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes, and shapes of particular anatomies or organs, and other features that would be discernable in the image based upon the skill and knowledge of the individual practitioner.

In addition to a CT number or Hounsfield value, an energy selective CT system can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known to have distinctly different atomic numbers, but at certain densities these two materials are indistinguishable by CT number alone.

An exemplary decomposition algorithm is employable to generate atomic number and density information from energy sensitive x-ray measurements. Exemplary multiple energy techniques comprise dual energy, photon counting energy discrimination, dual layered scintillation and/or one or more other techniques designed to measure x-ray attenuation in two or more distinct energy ranges. In an exemplary implementation, any compound or mixture of materials measured with a multiple energy technique may be represented as a hypothetical material having the same x-ray energy attenuation characteristics. This hypothetical material can be assigned an effective atomic number Z. Unlike the atomic number of an element, effective atomic number of a compound is defined by the x-ray attenuation characteristics, and it does not have to be an integer. This effective Z representation property stems from a well-known fact that x-ray attenuation in the energy range useful for diagnostic x-ray imaging is strongly related the electron density of compounds, which is also related to the atomic number of materials.

An exemplary implementation employs a measure of effective Z to differentiate x-ray attenuation differences in materials, for example, with increased accuracy and/or precision in BMD. An exemplary approach reduces numerical instability and provides calibration. An exemplary approach relates measured effective Z to a wide range of mixtures or compounds with higher accuracy.

An exemplary approach for calibration and decomposition of multiple energy x-ray measurements and/or EDCT/MECT/DE-CT into density and effective atomic number is presented. An exemplary approach determines effective atomic number and density to very precise values over a wide range of materials, for example, via a formulation that reduces a mathematical instability generally present in the problem solution. An exemplary approach employs a calibration of real materials to improve an accuracy of results.

Density and effective atomic number in an example are determined by BMD of x-ray data at two or more distinct energy bins and subsequent analysis of the material basis density image data. An exemplary approach determines a unique relationship between density and effective Z as a function of material basis functions, for example, through employment of calibration of known materials and a numerically stable formulation.

An exemplary implementation provides more accurate and precise effective Z information. An exemplary benefit comprises improvement in the differentiation of materials that are very close in effective Z over a wide range of effective Z.

An exemplary assumption is that, in the absence of K-edges, any material may be described as a linear combination of two other basis materials independent of a measurement system employed. An exemplary material decomposition comprises a non-linear beam hardening calibration that upon proper implementation and calibration, removes a system energy dependence. In an exemplary implementation, any material may be represented by a basis function pair. The basis function pair may be further represented by a unique effective Z (atomic number) and density.

An exemplary algorithm performs a decomposition of density and effective Z from multiple energy x-ray data, which hereafter may be referred to as rho(density)-Z (effective Z) imaging. Calibration in an example may be performed with real materials.

Figure 3:
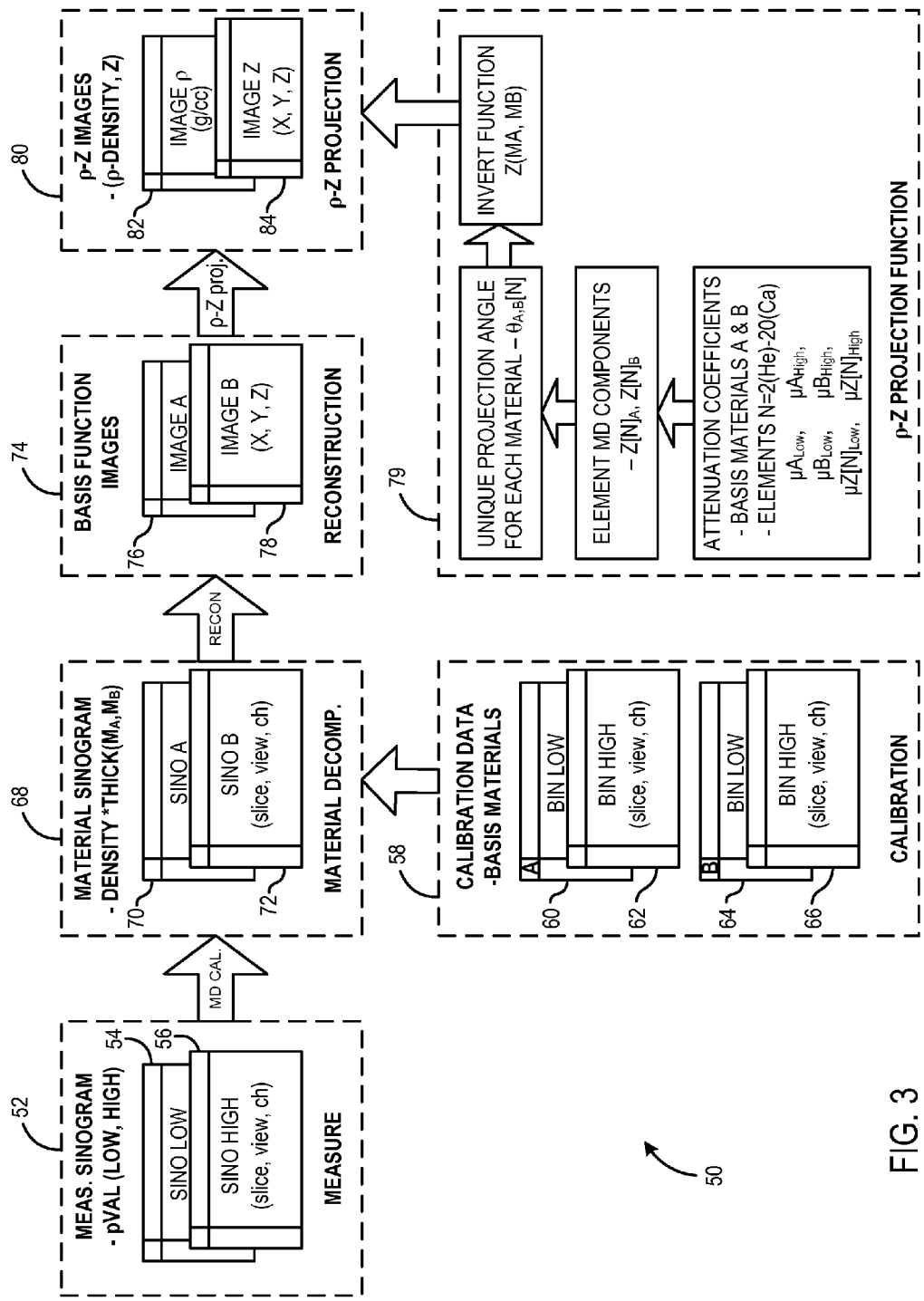
FIG. 3 is a block schematic diagram of a method to determine effective Z and material density according to an embodiment of the present invention.

FIG. 3 is a representation of exemplary logic 50 for decomposition of density and effective Z from multiple energy x-ray data. For example, logic 50 performs rho-Z imaging. STEP 52 in an example acquires projection data 54, 56 at two distinct energy ranges measured through the attenuation of the object, which, in general, is comprised of unknown material at unknown densities at the time of projection data acquisition. The low and high energy bins 54, 56 may be acquired through any number of approaches where two distinct energy ranges are used to measure the attenuation. Exemplary multiple energy techniques comprise dual energy, photon counting energy discrimination, dual layered scintillation and/or one or more other techniques designed to measure x-ray attenuation in two or more distinct energy ranges. The relationship between the basis material attenuation as a function of energy bin and path length is captured over the entire dynamic range of the object to be scanned.

STEP 58 in an example performs a number of actions for calibration that may occur before or after acquisition of projection data performed in STEP 52 described above. An algorithm and/or a user chooses a set of basis functions and/or materials, for example, water and aluminum. Calibration data is obtained by measuring the attenuation through the chosen basis materials, A and B, where the materials' densities are known. A calibration procedure is performed where the x-ray attenuation is measured as a function of each basis material for a low energy bin 60, 64 and a high energy bin 62, 66.

In one embodiment of the present invention, the number of actions performed for calibration in STEP 58 occur before acquisition of projection data performed in STEP 52 described above. It is contemplated that the calibration data may be stored to a database and retrieved when needed.

STEP 68 in an example performs material decomposition. STEP 68 in an example employs the measurement energy ranges from the object from STEP 52 and employs the calibration data from STEP 58 to perform the basis material decomposition. In one embodiment of the present invention, the basis material decomposition is performed using calibration data determined on-the-fly. In another embodiment of the present invention, the basis material decomposition is performed using stored calibration data recalled from a database or computer readable storage memory.

In one example of the present invention, a pair of tomographic sinograms 70, 72 representing the projected path lengths through the unknown object represented as two hypothetical objects comprised of the chosen basis materials are determined according to the following equation:

$$\begin{pmatrix} M_A \\ M_B \end{pmatrix} = \frac{\begin{pmatrix} B_H & -B_L \\ -A_H & A_L \end{pmatrix}\begin{pmatrix} M_L \\ M_H \end{pmatrix}}{(A_L B_H - A_H B_L)},$$ (Eqn. 1)

where $M_L$ and $M_H$ are data from low and high energy bins 54, 56, respectively, where $A_L$ and $A_H$ are data from low and high energy bins 60, 62, respectively, and where $B_L$ and $B_H$ are data from low and high energy bins 64, 66, respectively.

STEP 74 in an example performs reconstruction of the sonograms 70, 72 from STEP 68. For example, the sonograms 70, 72 are reconstructed through employment of exemplary and/or standard tomographic techniques to create a set of basis function images 76, 78.

STEP 79 in an example performs a number of actions that relate the basis materials' attenuation at the low and high energy bins 60-66 from the calibration data to function Z data $(Z[N]_A, Z[N]_B)$ of effective Z of the chosen basis materials A and B. It is contemplated that the number of actions performed in STEP 79 occur before or after acquisition of projection data performed in STEP 52 described above. In one embodiment of the present invention, the function Z data may be stored to a database and retrieved when needed.

Attenuation coefficients used in the relation include coefficients from basis materials A and B and elements N, where N in an example represents elements 2(He)-20(Ca). In an example, the attenuation coefficients include $\mu A_{Low}$, $\mu A_{High}$, $\mu B_{Low}$, $\mu B_{High}$, $\mu Z[N]_{Low}$, and $\mu Z[N]_{High}$. $Z[N]_A$ and $Z[N]_B$ are determined in an example according to the following equation:

$$\begin{pmatrix} Z_A \\ Z_B \end{pmatrix} = \frac{\begin{pmatrix} B_H & -B_L \\ -A_H & A_L \end{pmatrix}\begin{pmatrix} Z_L \\ Z_H \end{pmatrix}}{(A_L B_H - A_L B_H)},$$ (Eqn. 2)

where $Z_L$, $Z_H$, $A_L$, $A_H$, $B_L$, and $B_H$ include data from the attenuation coefficients.

Each material compound or mixture of materials $Z[N]_A$, $Z[N]_B$ in an example may be correlated to a unique function $\theta_{A,B}[N]$ of the atomic number of the basis materials through an analytical function of the ratio of materials $Z[N]_A$, $Z[N]_B$ according to the following equation:

$$\theta[N]=\arctan(Z_B[N]/Z_A[N])$$ (Eqn. 3).

An exemplary employment of the function arctan or arc tangent of the ratio of atomic numbers of basis materials serves to avoid numerical instability problems. Once the functional form is captured, an exemplary implementation inverts the unique function into an inverted function $Z(M_A, M_B)$ for processing the decomposed basis function images 76, 78 to form an image of the effective Z of the measured material as explained below. In one embodiment of the present invention, the inverted function data may be stored to a database and retrieved when needed.

In an embodiment of the present invention, the calibration data, function Z data and/or inverted function data are determined on-the-fly. In another embodiment, the calibration data, function Z data and/or inverted function data are recalled from a database or computer readable storage in memory.

STEP 80 in an example performs rho-Z projection. For example, STEP 80 analyzes the set of basis function images 76, 78 from STEP 74 to generate two new images of the object: density 82 and effective Z 84. To form the density image 82 in STEP 80, an exemplary implementation takes the sum of squares of the basis function images 76, 78 according to the following equation:

$$\rho_{Projection} = \frac{\sqrt{M_A^2 + M_B^2}}{\sqrt{W_A^2 + W_B^2}},$$ (Eqn. 4)

where $M_A$ and $M_B$ are data from basis function images 76, 78, respectively, and where $W_A$ and $W_B$ are corresponding basis function values for water. To form the effective Z image 84 in STEP 80, an effective Z fitting in an exemplary implementation employs a function arctan of data from the inverted analytic function $Z(M_A,M_B)$ according to the following equation:

$$Z_{Projection} = \mathbb{F}_{A,B}[\arctan(M_B/M_A)]$$ (Eqn. 5).

In an embodiment of the present invention, the density image 82 and the effective Z image 84 are displayed to a user. Alternatively, density image 82 and effective Z image 84 may be stored to a computer memory for storage and/or retrieval for displaying on a display. It is contemplated that logic 50 may store to a computer readable storage medium and/or display any or all data manipulation results or generated images affected thereby.

Figure 4:
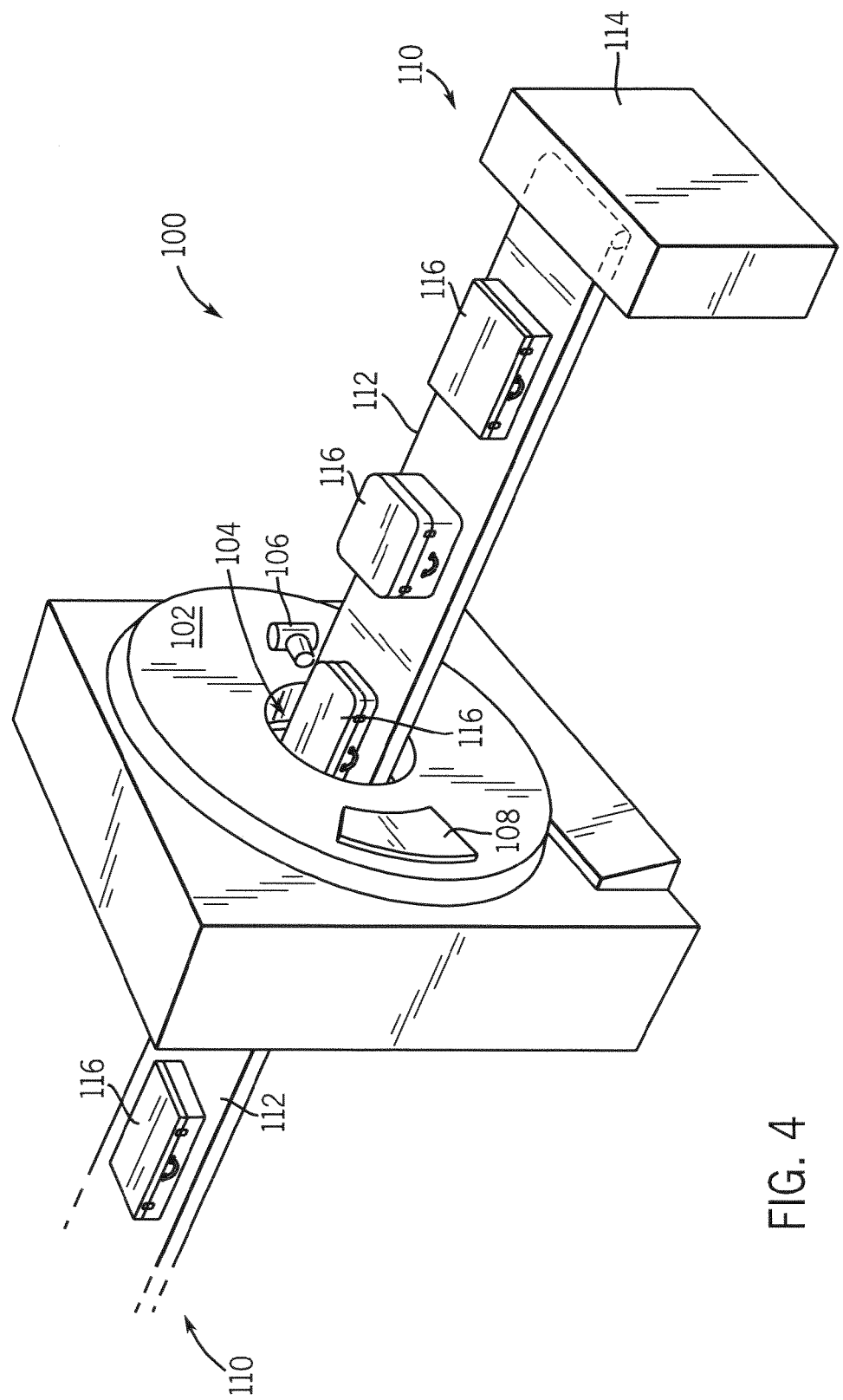
FIG. 4 is a pictorial view of a CT system for use with a non-invasive package inspection system.

Referring now to FIG. 4, package/baggage inspection system 100 includes a rotatable gantry 102 having an opening 104 therein through which packages or pieces of baggage may pass. The rotatable gantry 102 houses an x-ray and/or high frequency electromagnetic energy source 106 as well as a detector assembly 108 having scintillator arrays comprised of scintillator cells. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc. An exemplary implementation can aid in the development of automatic inspection techniques, such as explosive detection in luggage.

An implementation of the system 10 and/or 100 in an example comprises a plurality of components such as one or more of electronic components, hardware components, and/or computer software components. A number of such components can be combined or divided in an implementation of the system 10 and/or 100. An exemplary component of an implementation of the system 10 and/or 100 employs and/or comprises a set and/or series of computer instructions written in or implemented with any of a number of programming languages, as will be appreciated by those skilled in the art. An implementation of the system 10 and/or 100 in an example comprises any (e.g., horizontal, oblique, or vertical) orientation, with the description and figures herein illustrating an exemplary orientation of an implementation of the system 10 and/or 100, for explanatory purposes.

An implementation of the system 10 and/or the system 100 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the system 10 and/or the system 100 comprises the recordable data storage medium of the image reconstructor 34, and/or the mass storage device 38 of the computer 36. A computer-readable signal-bearing medium for an implementation of the system 10 and/or the system 100 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory.

Therefore, according to an embodiment of the present invention, a diagnostic imaging system includes a high frequency electromagnetic energy source that emits a beam of high frequency electromagnetic energy toward an object to be imaged, a detector that receives high frequency electromagnetic energy emitted by the high frequency electromagnetic energy source and attenuated by the object, and a data acquisition system (DAS) operably connected to the detector. A computer is operably connected to the DAS and programmed to acquire projection data from the detector of an unknown material at the time of projection data acquisition. The computer is also programmed to generate a density image for the unknown material based on a calibration of two or more known basis materials and to generate an effective atomic number (Z) for the unknown material based on the calibration of two or more known basis materials and based on a function arctan of a ratio of atomic numbers of the two or more known basis materials. The density and effective atomic number images are stored to a computer readable storage medium.

According to another embodiment of the present invention, a method of diagnostic imaging includes acquiring multi-energy range x-ray data attenuated by an object comprising an unknown material and separating the multi-energy range x-ray data into at least two energy bins. The method also includes calibrating a plurality of basis materials and determining an arc tangent of a ratio of atomic numbers of the plurality of basis materials. A density image of the unknown material based on the calibration is generated, and an effective Z image of the unknown material based on the calibration and the arc tangent determination is generated. The method includes storing the density and effective Z images to computer memory.

According to yet another embodiment of the present invention, a computer readable storage medium includes instructions stored thereon that, when executed by a processor, causes the computer to acquire x-ray projection data of an unknown material and acquire calibration data of a pair of known materials. The instructions further cause the computer to display a reconstructed density image for the unknown material to a user, the density image generated from a reconstruction based on the calibration data and display a reconstructed effective Z image for the unknown material to a user, the effective Z image generated from a reconstruction based on the calibration data and based on arc tangent data of a ratio of atomic numbers of the pair of known materials.

The present invention has been described in terms of the preferred embodiment, and it is recognized that equivalents, alternatives, and modifications, aside from those expressly stated, are possible and within the scope of the appending claims.

What is claimed is:

1. A diagnostic imaging system, comprising:
    a high frequency electromagnetic energy source that emits a beam of high frequency electromagnetic energy toward an object to be imaged;
    a detector that receives high frequency electromagnetic energy emitted by the high frequency electromagnetic energy source and attenuated by the object;
    a data acquisition system (DAS) operably connected to the detector; and
    a computer operably connected to the DAS and programmed to:
        acquire projection data from the detector of an unknown material at the time of projection data acquisition;
        generate a density image for the unknown material based on a sum of squares of basis function images;
        derive a ratio $Z(N)_A/Z(N)_B$ of atomic numbers of known basis materials $(N)_A$ and $(N)_B$;
        generate an effective atomic number (Z) for the unknown material based on the density images of at least two known basis materials $(N)_A$ and $(N)_B$ and based on a function $\arctan(Z(N)_A/Z(N)_B)$ of the ratio $Z(N)_A/Z(N)_B$ of atomic numbers; and
        store the density and effective atomic number images to a computer readable storage medium.

2. The diagnostic imaging system of claim 1, wherein the detector comprises an EDCT detector that provides energy sensitive measurements of the high frequency electromagnetic energy emitted by the high frequency electromagnetic energy source; and
    wherein the computer operably connected to the DAS is further programmed to employ a basis material decomposition algorithm to generate the effective atomic number (Z) and density images for the unknown material from the energy sensitive measurements.

3. The diagnostic imaging system of claim 2, wherein the EDCT detector serves to measure x-ray attenuation in two or more distinct energy ranges; and wherein the computer operably connected to the DAS is further programmed to represent any compound or mixture of materials of the unknown material measured with the EDCT detector by a hypothetical material that comprises energy attenuation characteristics that are substantially the same as the effective atomic number (Z) for the unknown material.

4. The diagnostic imaging system of claim 1, wherein the computer operably connected to the DAS is further programmed to employ the effective atomic number (Z) to differentiate components of the unknown material with increased accuracy and/or precision in basis material decomposition (BMD).

5. The diagnostic imaging system of claim 4, wherein the computer operably connected to the DAS is further programmed to differentiate the components of the unknown material notwithstanding a closeness in their individual atomic numbers (Z) over a wide range of atomic numbers (Z).

6. The diagnostic imaging system of claim 1, wherein the computer operably connected to the DAS is further programmed to perform at least one of effective Z fitting and generating density and effective Z images of the object to be imaged.

7. The diagnostic imaging system of claim 1, wherein the computer operably connected to the DAS is further programmed to measure attenuation as a function of the unknown material for a low energy bin and a high energy bin.

8. The diagnostic imaging system of claim 7, wherein the computer operably connected to the DAS is further programmed to capture, over an entire dynamic range of the object to be imaged, a relationship between:

the attenuation as the function of the unknown material for the low energy bin and the high energy bin; and attenuation as a function of path length for the unknown material.

9. The diagnostic imaging system of claim 1, wherein the computer operably connected to the DAS is further programmed to perform material decomposition that comprises a set of two tomographic sinograms representing projected path lengths through the object to be scanned represented as two hypothetical objects of the two or more known basis materials.

10. The diagnostic imaging system of claim 1, wherein the computer operably connected to the DAS is further programmed to relate attenuation of the two or more known basis materials at a low energy bin and a high energy bin from calibration data to a linear function of effective Z of the two or more known basis materials.

11. The diagnostic imaging system of claim 1, wherein the computer operably connected to the DAS is further programmed to invert an analytic function and process decomposed basis function images to form the image of the effective atomic number Z of the unknown material.

12. The diagnostic imaging system of claim 11, wherein the computer operably connected to the DAS is further programmed to process the decomposed basis function images to form the image of the density of the unknown material.

13. A method of diagnostic imaging comprising:

acquiring multi-energy range x-ray data attenuated by an object comprising an unknown material;

separating the multi-energy range x-ray data into at least a high energy bin and a low energy bin;

calibrating a plurality of basis materials;

deriving a ratio $Z(N)_A/Z(N)_B$ of atomic numbers of at least two of the basis materials $(N)_A$ and $(N)_B$;

determining an arc tangent of a ratio $Z(N)_A/Z(N)_B$ of atomic numbers of the at least two basis materials $(N)_A$ and $(N)_B$;

generating a density image of the unknown material based on a sum of squares of basis function images;

generating an effective Z image of the unknown material based on the calibration and the determination of the function $\arctan(Z(N)_A/Z(N)_B)$; and storing the density and effective Z images to computer memory.

14. The method of claim 13 wherein calibrating the plurality of basis materials comprises:

measuring x-ray attenuation through the plurality of basis materials; and separating the measured x-ray attenuation into one of the low energy bin and the high energy bin for each of the plurality of basis materials.

15. The method of claim 14 further comprising performing a basis material decomposition based on each of the at least two energy bins of the multi-energy range x-ray data and the low and high energy bins of each of the plurality of basis materials.

16. The method of claim 15 wherein the basis material decomposition into first material data $M_A$ and second material data $M_B$ is determined by evaluating a ratio having, as a numerator, the product of a 2×2 matrix with a 1×2 matrix and having, as a denominator, the difference of two products, where the terms in the ratio include data from the low and high energy bins of each of the plurality of basis materials according to the expression:

$$\begin{pmatrix} M_A \\ M_B \end{pmatrix} = \frac{\begin{pmatrix} B_H & -B_L \\ -A_H & A_L \end{pmatrix} \begin{pmatrix} M_L \\ M_H \end{pmatrix}}{(A_L B_H - A_H B_L)}.$$

wherein $A_H$, $B_H$, and $M_H$ are data from the high energy bin and $A_L$, $B_L$, and $M_L$ are data from the low energy bin.

17. The method of claim 14 further comprising reconstructing a basis function image based for each of the basis material decompositions.

18. The method of claim 17 wherein generating the density image of the unknown material comprises generating a rho projection based on the basis function images, where the rho projection includes a ratio having square root expressions for both numerator and denominator, the terms in the ratio including first material data $M_A$ and second material data $M_B$ and corresponding basis function values for water $W_A$ and $W_B$, according to the expression:

$$\rho_{Projection} = \frac{\sqrt{M_A^2 + M_B^2}}{\sqrt{W_A^2 + W_B^2}}.$$

19. The method of claim 17 wherein generating the effective Z image of the unknown material comprises generating an effective Z projection based on an arctangent function having a first material data $M_A$ term and a second material data $M_B$ term, according to the expression:

$$Z_{projection} = F_{A,B}[\arctan(M_B/M_A)].$$

20. The method of claim 14 wherein determining the arc tangent comprises relating attenuation coefficients of the low and high energy bins of the plurality of basis materials and an element N to a function of effective Z of the plurality of basis materials.

21. The method of claim 20 wherein relating the attenuation coefficients comprises relating attenuation coefficients $Z_A$ and $Z_B$ by evaluating a ratio having, as a numerator, the product of a 2×2 matrix with a 1×2 matrix and having, as a denominator, the difference of two products, where the terms in the ratio include data from the attenuation coefficients according to the expression:

$$\begin{pmatrix} Z_A \\ Z_B \end{pmatrix} = \frac{\begin{pmatrix} B_H & -B_L \\ -A_H & A_L \end{pmatrix}\begin{pmatrix} Z_L \\ Z_H \end{pmatrix}}{(A_L B_H - A_L B_L)}.$$

wherein $A_H$, $B_H$, and $Z_H$ are data from the high energy bin and $A_L$, $B_L$, and $Z_L$ are data from the low energy bin.

22. The method of claim 21 wherein determining the arc tangent further comprises correlating the related attenuation coefficients to a unique function having atomic numbers of the attenuation coefficients $Z_A$ and $Z_B$, according to the expression:

$$\theta[N] = \arctan(Z_B[N]/Z_A[N]).$$

23. The method of claim 20 wherein element N has an effective atomic number in the range of 2-20.

24. A computer readable storage medium having stored thereon instructions that, when executed by a processor, causes the computer to:
acquire x-ray projection data of an unknown material;
acquire calibration data of a pair of known materials $(N)_A$ and $(N)_B$;
display a reconstructed density image for the unknown material to a user, the density image generated from a reconstruction based on a sum of squares of basis function images; and
display a reconstructed effective Z image for the unknown material to a user, the effective Z image generated from a reconstruction further based on the calibration data and on a function $\arctan(Z(N)_A/Z(N)_B)$ of a ratio $Z(N)_A/Z(N)_B$ of atomic numbers of the pair of known materials $(N)_A$ and $(N)_B$.

25. The computer readable storage medium of claim 24 wherein the instructions that cause the computer to acquire the calibration data cause the computer to acquire the calibration data from a database.

26. The computer readable storage medium of claim 24 wherein the instructions further cause the computer to acquire the arc tangent data of a ratio of atomic numbers from a database.

27. The computer readable storage medium of claim 26 wherein the instructions further cause the computer to:
invert the function $\arctan(Z(N)_A/Z(N)_B)$; and
perform an effective Z fitting based on a basis function image of the projection data and the inverted arc tangent function.

* * * * *

UNITED STATES PATENT AND TRADEMARK OFFICE
CERTIFICATE OF CORRECTION

PATENT NO. : 7,697,657 B2 Page 1 of 1
APPLICATION NO. : 11/690245
DATED : April 13, 2010
INVENTOR(S) : Walter et al.

It is certified that error appears in the above-identified patent and that said Letters Patent is hereby corrected as shown below:

In Column 7, Line 65, delete "$\mu Z[N]L_{LOW},$" and insert -- $\mu Z[N]_{LOW},$ --, therefor.

In Column 12, Lines 36-38, in Claim 16, after " $\begin{pmatrix} M_A \\ M_B \end{pmatrix} = \dfrac{\begin{pmatrix} B_H & -B_L \\ -A_H & A_L \end{pmatrix}\begin{pmatrix} M_L \\ M_H \end{pmatrix}}{(A_L B_H - A_H B_L)}$ " delete ".".

In Column 12, Line 63, in Claim 19, delete "arctangent" and insert -- arc tangent --, therefor.

In Column 13, Lines 16-19, in Claim 21, after " $\begin{pmatrix} Z_A \\ Z_B \end{pmatrix} = \dfrac{\begin{pmatrix} B_H & -B_L \\ -A_H & A_L \end{pmatrix}\begin{pmatrix} Z_L \\ Z_H \end{pmatrix}}{(A_L B_H - A_L B_H)}$ " delete ".".

Signed and Sealed this

Fifteenth Day of June, 2010

David J. Kappos
*Director of the United States Patent and Trademark Office*